US008906422B2

(12) United States Patent
Kwong

(10) Patent No.: US 8,906,422 B2
(45) Date of Patent: Dec. 9, 2014

(54) METHOD FOR INHIBITING CANCER USING ARSENIC TRIOXIDE

(75) Inventor: Yok-Lam Kwong, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 729 days.

(21) Appl. No.: 11/871,068

(22) Filed: Oct. 11, 2007

(65) Prior Publication Data

US 2008/0085931 A1 Apr. 10, 2008

Related U.S. Application Data

(63) Continuation-in-part of application No. 10/669,869, filed on Sep. 23, 2003, now Pat. No. 7,521,071, and a continuation-in-part of application No. 11/549,347, filed on Oct. 13, 2006, now abandoned.

(60) Provisional application No. 60/417,200, filed on Oct. 9, 2002, provisional application No. 60/483,014, filed on Jun. 25, 2003.

(51) Int. Cl.
A61K 33/36 (2006.01)
A61P 35/00 (2006.01)

(52) U.S. Cl.
CPC ..................................... A61K 33/36 (2013.01)
USPC ........................................................ 424/623

(58) Field of Classification Search
None
See application file for complete search history.

(56) References Cited

U.S. PATENT DOCUMENTS

| 6,723,351 B2 * | 4/2004 | Warrell et al. ................. 424/623 |
| 6,875,451 B2 * | 4/2005 | Ellison et al. .................. 424/623 |
| 7,521,071 B2 | 4/2009 | Kumana et al. |
| 2002/0013371 A1 * | 1/2002 | Warrell et al. ................. 514/623 |
| 2004/0126434 A1 | 7/2004 | Kumana et al. |
| 2008/0089949 A1 | 4/2008 | Kwong |
| 2008/0089951 A1 | 4/2008 | Kwong |
| 2008/0166425 A1 | 7/2008 | Kwong |

FOREIGN PATENT DOCUMENTS

| CN | 1370540 | 9/2002 |
| CN | 1546059 | 11/2004 |
| WO | WO 99/24029 | 5/1999 |

OTHER PUBLICATIONS

Arber et al., Cancer Research (1997), vol. 57, pp. 1569-1574.*
Li et al., Abstract of Pancreas (2003), vol. 27, No. 2, pp. 174-179.*
Moustafa et al., Oncogene (2004), vol. 23, pp. 5252-5256.*
Jaffe et al., Blood (2008), vol. 112, pp. 4384-4399.*
STN online, file LIFESCI, Ac. No. 2009:195259 (Cheung, (2006) vol. 68, No. 07, The molecular mechanisms of arsenic trioxide), Abstract.*
Au et al., Preliminary experience of oral arsenic trioxide based therapy in the treatmnet of refractory mantle cell lymphoma, Annals of Oncology (Jun. 2005), vol. 16, Supp. [5], p. 136, MA 338.*
Cheung, (2006) vol. 68, No. 07, The molecular mechanisms of arsenic trioxide, Abstract.*
Rojewski et al., Dual effects of arsenic trioxide (As2O3) on non-acute promyelocytic leukaemia myeloid cell lines: induction of apoptosis and inhibition of proliferation, British Journal of Haematology (2002), vol. 116, pp. 555-563.*
Abroun, et al., "Receptor synergy of interleukin-6 (IL-6) and insulin-like growth factor-I in myeloma cells that highly express IL-6 receptor alpha [corrected]", Blood, 103(6):2291-8 (2004).
Akay and Gazitt, "Arsenic trioxide selectively induces early and extensive apoptosis via the APO2/caspase-8 pathway engaging the mitochondrial pathway in myeloma cells with mutant p53", Cell Cycle, 2(4):358-68 (2003).
Alt, et al., "Phosphorylation-dependent regulation of cyclin D1 nuclear export and cyclin D1-dependent cellular transformation" Genes Dev, 14:3102-14 (2000).
Au, et al., "Combined arsenic trioxide and all-trans retinoic acid treatment for acute promyelocytic leukaemia recurring from previous relapses successfully treated using arsenic trioxide", Br J Haematol., 117(1):130-2 (2002).
Au, et al., "Oral arsenic trioxide in the treatment of relapsed acute promyelocytic leukemia", Blood, 102:407-8 (2003).
Au, et aal., "Treatment of relapsed acute promyelocytic leukemia by arsenic-based strategies without hematopoietic stem cell transplantation in Hong Kong: A Seven-year experience", Blood (ASH Annual Meeting Abstracts), 104:Abstract 395 (2004).
Au, et al., "Successful treatment of relapsed acute promyelocytic leukemia in a patient receiving continuous ambulatory peritoneal dialysis with oral arsenic trioxide", Arch Intern Med., 165(9):1067-8 (2005).
Au, et al., "Elemental arsenic entered the cerebrospinal fluid during oral arsenic trioxide treatment of meningeal relapse of acute promyelocytic leukemia", Blood, 107(7):3012-3 (2006).
Bahlis, et al., "Feasibility and correlates of arsenic trioxide combined with ascorbic acid-mediated depletion of intracellular glutathione for the treatment of relapsed/refractory multiple myeloma", Clin Cancer Res., 8(12):3658-68 (2002).
Berenson, et al., "A prospective, open-label safety and efficacy study of combination treatment with melphalan, arsenic trioxide, and ascorbic acid in patients with relapsed or refractory multiple myeloma", Clin Lymphoma, 5(2):130-4 (2004).
Burke, et al., "BMS-345541 is a highly selective inhibitor of I kappa B kinase that binds at an allosteric site of the enzyme and blocks NF-kappa B-dependent transcription in mice", J Biol Chem, 278:1450-6 (2003).

(Continued)

Primary Examiner — Abigail Fisher
Assistant Examiner — Frank Choi
(74) Attorney, Agent, or Firm — Pabst Patent Group LLP

(57) ABSTRACT

The invention provides a method for treating cancers that are dependent on cyclin D1 for proliferation, survival, metastasis and differentiation, involving administering a composition containing an effective amount of arsenic trioxide to an affected patient. The arsenic trioxide can be administered orally, for example, as a solution, suspension, syrup, emulsion, tablet, or capsule. The composition can also contain one or more pharmaceutically acceptable carriers and/or excipients.

4 Claims, 11 Drawing Sheets

(56) References Cited

OTHER PUBLICATIONS

Camacho, et al., "Leukocytosis and the retinoic acid syndrome in patients with acute promyelocytic leukemia treated with arsenic trioxide", *J. CLin. Oncol.*, 18:2620-5 (2000).
Carpenter, "Employment of the epidermal growth factor receptor in growth factor-independent signaling pathways", *J Cell Biol.*, 146(4):697-702 (1999).
Catley, et al., "Perspectives for combination therapy to overcome drug-resistant multiple myeloma", *Drug Resist Updat.*, 8(4):205-18 (2005).
Chen, et al., "Use of arsenic trioxide (As2O3) in the treatment of acute promyelocytic leukemia (APL): I. As2O3 exerts dose-dependent dual effects on APL cells" *Blood*, 89(9):3345-53 (1997).
Choong and Cohen, "Epidermal growth factor receptor directed therapy in head and neck cancer", *Crit Rev Oncol Hematol.*, 57(1):25-43 (2006).
Cohen, et al., "The expanding role of systemic therapy in head and neck cancer", *J Clin Oncol.*, 22(9):1743-52 (2004).
Cole, et al., "Further evidence that the tyrosine phosphorylation of glycogen synthase kinase-3 (GSK3) in mammalian cells is an autophosphorylation event", *Biochem J.*, 377:249-55 (2004).
Cross, et al., "Inhibition of glycogen synthase kinase-3 by insulin mediated by protein kinase B", *Nature*, 378:785-9 (1995).
Davison, et al., "JNK activation is a mediator of arsenic trioxide-induced apoptosis in acute promyelocytic leukemia cells", *Blood*, 103(9):3496-502 (2004).
Del Razo, et al., "Stress proteins induced by arsenic", *Toxicol Appl Pharmacol.*, 177(2):132-48 (2001).
Diehl, et al., "Glycogen synthase kinase-3beta regulates cyclin D1 proteolysis and subcellular localization", *Genes Dev*,12:3499-511 (1998).
Diehl, et al., "Inhibition of cyclin D1 phosphorylation on threonine-286 prevents its rapid degradation via the ubiquitin-proteasome pathway", *Genes Dev*, 11:957-72 (1997).
Fan, et al., "Phospholipase C-independent activation of glycogen synthase kinase-3beta and C-terminal Src kinase by Galphaq", *J Biol Chem*, 278:52432-6 (2003).
Ferlin, et al., "Insulin-like growth factor induces the survival and proliferation of myeloma cells through an interleukin-6-independent transduction pathway", *Br J Haematol.*, 111(2):626-34 (2000).
Forstpointer, et al. "The addition of rituximab to a combination of fludarabine, cyclophosphamide, mitoxantrone (FCM) significantly increases the response rate and prolongs survival as compared with FCM alone in patients with relapsed and refractory follicular and mantle cell lymphomas: results of a prospective randomized study of the German Low-Grade Lymphoma Study Group" *Blood*, 104:3064-71 (2004).
Gartenhaus, et al., "Arsenic trioxide cytotoxicity in steroid and chemotherapy-resistant myeloma cell lines: enhancement of apoptosis by manipulation of cellular redox state", *Clin Cancer Res.*, 8(2):566-72 (2002).
Goy, et al., "Phase II study of proteasome inhibitor bortezomib in relapsed or refractory B-cell non-Hodgkin's lymphoma" *J Clin Oncol*, 23:667-75 (2005).
Grandis, et al., "Levels of TGF-alpha and EGFR protein in head and neck squamous cell carcinoma and patient survival", *J Natl Cancer Inst.*, 90:824-32 (1998).
Guo, et al., "Phosphorylation of cyclin D1 at Thr 286 during S phase leads to its proteasomal degradation and allows efficient DNA synthesis" *Oncogene*, 24:2599-612 (2005).
Guo, et al., "Post-transcriptional regulation of cyclin D1 expression during G2 phase" *Oncogene*, 21:7545-56 2002).
Hartigan, et al., "Glycogen synthase kinase 3beta is tyrosine phosphorylated by PYK2", *Biochem Biophys Res Commun.*, 284:485-9 (2001).
Hartigan, et al., "Transient increases in intracellular calcium result in prolonged site-selective increases in Tau phosphorylation through a glycogen synthase kinase 3beta-dependent pathway", *J Biol Chem*, 274:21395-401 (1999).

Hicke, "Protein regulation by monoubiquitin", *Nat Rev Mol Cell Biol*, 2:195-201 (2001).
Huang, et al., "Acute and chronic arsenic poisoning associated with treatment of acute promyelocytic leukaemia", *Br J Haematol.*, 103(4):1092-5 (1998).
Hubbard and Till, "Protein tyrosine kinase structure and function", *Annu Rev Biochem.*, 69:373-98 (2000).
Hughes, et al., "Modulation of the glycogen synthase kinase-3 family by tyrosine phosphorylation", *EMBO J*, 12:803-8 (1993).
Hussein, et al., "Phase 2 study of arsenic trioxide in patients with relapsed or refractory multiple myeloma", *Br J Haematol.*, 125(4):470-6 (2004).
Janne, "Ongoing first-line studies of epidermal growth factor receptor tyrosine kinase inhibitors in select patient populations", *Semin Oncol.*, 32(6 Suppl 10):S9-15 (2005).
Jemal, et al., "Cancer statistics, 2005", *CA Cancer J Clin.*, 55(1):10-30 (2005).
Kauffmann-Zeh, et al., "Suppression of c-Myc-induced apoptosis by Ras signalling through PI(3)K and PKB", *Nature*, 385:544-8 (1997).
Kaufmann, et al., "Antitumor activity of rituximab plus thalidomide in patients with relapsed/refractory mantle cell lymphoma", *Blood*, 104:2269-71 (2004).
Kim, et al., "The novel tyrosine kinase ZAK1 activates GSK3 to direct cell fate specification", *Cell*, 99:399-408 (1999).
Kumana, et al., "Systemic availability of arsenic from oral arsenic-trioxide used to treat patients with hematological malignancies", *Eur J Clin Pharmacol.*, 58(8):521-6 (2002).
Kwak, et al., "IkappaB kinase alpha regulates subcellular distribution and turnover of cyclin D1 by phosphorylation", *J Biol Chem*, 280:33945-52 (2005).
Kwong, et al., "Delicious poison: arsenic trioxide for the treatment of leukemia", *Blood*, 89(9):3487-8 (1997).
Kwong, et al., "Arsenic trioxide- and idarubicin-induced remissions in relapsed acute promyelocytic leukaemia: clinicopathological and molecular features of a pilot study", *Am J. Hematol.*, 66:274-9 (2001).
Kwong, "Arsenic trioxide in the treatment of haematological malignancies", *Expert Opin Drug Saf.*, 3(6):589-97 (2004).
Lalemand-Breitenbach, et al., "Role of promyelocytic leukemia (PML) sumolation in nuclear body formation, 11S proteasome recruitment, and As2O3-induced PML or PML/retinoic acid receptor alpha degradation", *J Exp Med.*, 193(12):1361-71 (2001).
Lenz, et al., "Immunochemotherapy with rituximab and cyclophosphamide, doxorubicin, vincristine, and prednisone significantly improves response and time to treatment failure, but not long-term outcome in patients with previously untreated mantle cell lymphoma: results of a prospective randomized trial of the German Low Grade Lymphoma Study Group (GLSG)", *J Clin Oncol.*, 23:1984-92 (2005).
Lesort, et al., "Insulin transiently increases tau phosphorylation: involvement of glycogen synthase kinase-3beta and Fyn tyrosine kinase", *J Neurochem*, 72:576-84 (1999).
Ling, et al., "NF-kappaB-inducing kinase activates IKK-alpha by phosphorylation of Ser-176", *Proc Natl Acad Sci U S A.*, 95:3792-7 (1998).
Liu, et al., "Arsenic trioxide-induced apoptosis in myeloma cells: p53-dependent G1 or G2/M cell cycle arrest, activation of caspase-8 or caspase-9, and synergy with APO2/TRAIL.", *Blood*, 101(10):4078-87 (2003).
Lu, et al., "Tetra-arsenic tetra-sulfide for the treatment of acute promyelocytic leukemia: a pilot report", *Blood*, 99(9):3136-43 (2002).
Malinin, et al., "MAP3K-related kinase involved in NF-kappaB induction by TNF, CD95 and IL-1", *Nature*, 385:540-4 (1997).
Marmor and Yarden, "Role of protein ubiquitylation in regulating endocytosis of receptor tyrosine kinases", *Oncogene*, 23(11):2057-70 (2004).
Mosesson, et al., "Endocytosis of receptor tyrosine kinases is driven by monoubiquitylation, not polyubiquitylation", *J Biol Chem.*, 278(24):21323-6 (2003).
Munshi, "Arsenic trioxide: an emerging therapy for multiple myeloma", *Oncologist*, 6 Suppl 2:17-21 (2001).

(56) References Cited

OTHER PUBLICATIONS

Ni, et al., "Pharmacokinetics of intravenous arsenic trioxide in the treatment of acute promyelocytic leukemia", *Chin Med J (Engl).*, 111(12):1107-10 (1998).
Niu, et al., "Studies on treatment of acute promyelocytic leukemia with arsenic trioxide: remission induction, follow-up, and molecular monitoring in 11 newly diagnosed and 47 relapsed acute promyelocytic leukemia patients", *Blood*, 94(10):3315-24 (1999).
O'Connor, et al.,"Phase II clinical experience with the novel proteasome inhibitor bortezomib in patients with indolent non-Hodgkin's lymphoma and mantle cell lymphoma", *J Clin Oncol*, 23:676-84 (2005).
Ohnishi, et al., "Prolongation of the QT interval and ventricular tachycardia in patients treated with arsenic trioxide for acute promyelocytic leukemia", *Ann Intern Med.*, 133(11):881-5 (2000).
Park, et al., "Arsenic trioxide-mediated growth inhibition in MC/CAR myeloma cells via cell cycle arrest in association with induction of cyclin-dependent kinase inhibitor, p21, and apoptosis", *Cancer Res.*, 60(11):3065-71 (2000).
Pomerantz and Grandis, "The epidermal growth factor receptor signaling network in head and neck carcinogenesis and implications for targeted therapy", *Semin Oncol.*, 31(6):734-43 (2004).
Qian, et al., "New perspectives in arsenic-induced cell signal transduction", *J Inorg Biochem.*, 96(2-3):271-8 (2003).
Qiang, et al., "Insulinlike growth factor-I signaling in multiple myeloma: downstream elements, functional correlates, and pathway cross-talk", *Blood*, 99(11):4138-46 (2002).
Romaquera, et al., "High rate of durable remissions after treatment of newly diagnosed aggressive mantle-cell lymphoma with rituximab plus hyper-CVAD alternating with rituximab plus high-dose methotrexate and cytarabine" *J Clin Oncol*, 23:7013-23 (2005).
Roodman, "Pathogenesis of myeloma bone disease", *Blood Cells Mol Dis.*, 32(2):290-2 (2004).
Sayas, et al., "GSK-3 is activated by the tyrosine kinase Pyk2 during LPA1-mediated neurite retraction", *Mol Biol Cell*, 17:1834-44 (2006).
Shen, et al., "Use of arsenic trioxide (As2O3) in the treatment of acute promyelocytic leukemia (APL): II. Clinical efficacy and pharmacokinetics in relapsed patients", *Blood*, 89(9):3354-60 (1997).
Sherr, "Cancer cell cycles" *Science*, 274:1672-7 (1996).
Sherr, et al., "The RB and p53 pathways in cancer" *Cancer Cell*, 2:103-112 (2002).
Simeonova, et al., "c-Src-dependent activation of the epidermal growth factor receptor and mitogen-activated protein kinase pathway by arsenic. Role in carcinogenesis", *J Biol Chem.*, 277(4):2945-50 (2002).
Siu, et al., Effects of oral arsenic trioxide therapy on QT intervals in patients with acute promyelocytic leukemia: implications for long-term cardiac safety, *Blood*, 108(1):103-6 (2006).
Soignet, et al., "Complete remission after treatment of acute promyelocytic leukemia with arsenic trioxide", *N Engl J Med.*, 339(19):1341-8 (1998).
Soignet, et al., "United States multicenter study of arsenic trioxide in relapsed acute promyelocytic leukemia", *J Clin Oncol.*, 19(18):3852-60 (2001).
Sternsdorf, et al., PIC-1/SUMO-1-modified PML-retinoic acid receptor alpha mediates arsenic trioxide-induced apoptosis in acute promyelocytic leukemia, *Mol Cell Biol.*, 19(7):5170-8 (1999).
Swerdlow, et al., Mantle Cell Lymphoma, in Jaffe, E.S. et al. Ied.), WHO Classification of Tumors, (2001) 168-170.

Tai, et al., "Insulin-like growth factor-1 induces adhesion and migration in human multiple myeloma cells via activation of beta1-integrin and phosphatidylinositol 3'-kinase/AKT signaling", *Cancer Res.*, 63(18):5850-8 (2003).
Tallman, et al., "Acute promyelocytic leukemia: evolving therapeutic strategies", *Blood*, 99(3):759-67 (2002).
The Non-Hodgkin's Lymphoma Classification Project. A clinical evaluation of the International Lymphoma Study Group classification of non-Hodgkin's lymphoma, *Blood*, 89:3909-3918 (1997).
Tsujimoto, et al., "Clustering of breakpoints on chromosome 11 in human B-cell neoplasms with the t(11;14) chromosome translocation", *Nature*, 315:340-3 (1985).
Tsujimoto, et al., "Molecular cloning of the chromosomal breakpoint of B-cell lymphomas and leukemias with the t(11;14) chromosome translocation" *Science*, 224:1403-6 (1994).
Van De Donk, et al., "Growth factors and antiapoptotic signaling pathways in multiple myeloma", *Leukemia*, 19(12):2177-85 (2005).
Vanhaesebroeck, et al., "Phosphoinositide 3-kinases: a conserved family of signal transducers", *Trends Biochem Sci*, 22:267-72 (1997).
Witzig "Current treatment approaches for mantle-cell lymphoma", *J Clin Oncol*, 23:6409-14 (2005).
Witzig, et al., "Phase II trial of single-agent temsirolimus (CCI-779) for relapsed mantle cell lymphoma", *J Clin Oncol*, 23:5347-56 (2005).
Yamauchi, et al., "Metabolism and excretion of orally administered arsenic trioxide in the hamster", *Toxicology*, 34(2):113-21 (1985).
Yang and Frenkel, "Arsenic-mediated cellular signal transduction, transcription factor activation, and aberrant gene expression: implications in carcinogenesis", *Environ Pathol Toxicol Oncol.*, 21(4):331-42 (2002).
Hyun, et al., "Arsenic trioxide inhibits the growth of A498 renal cell carcinoma cells via cell cycle arrest or apoptosis", *Biochem. Biophys. Res. Comm.*, 300:230-235 (2003).
Nie, et al., "Studies of apoptosis induced malignant lymphoma cell lines by arsenic trioxide", *Tumor (Shanghai)*, 21(2):79-82 (2001).
Tang, et al., "Inhibitory effect of arsenictrioxide on proliferation of hepatoma cells in mice", *World Clin J. Dig.*, 13(17):2074-2077 (2005).
Remington's Pharmaceutical Sciences (17th Ed. 1985), pp. 201.301.
Seol, et al., "Potential role of caspase-3 and -9 in arsenic trioxide-mediated apoptosis in PCI-1 head and neck cancer cells", *Int J Oncol.*, 18(2):249-55 (2001).
Shui, et al., "Cyclin D1 and mantle cell lymphoma", *J. Clin. Exp. Pathol.*, 18(1):86-87 (2002).
Zhao, et al., "Effect of AS203 on cyclins D1 and B1 expression in tow glioblastoma cell lines differing in p53 status", *Clin. J Neurosurg.*, 20(3):202-206 (2004).
Douer and Tallman, "Arsenic trioxide: new clinical experience with an old medication in hematologic malignancies," *J. Clinical Oncology*, 23(10): 2396-2410 (2005).
Müller-Tidow, et al., "High-throughput analysis of genome-wide receptor tyrosine kinase expression in human cancers identifies potential novel drug targets," *Clinical Cancer Research*, 10(4):1241-9 (2004).
Rousselot, et al., Arsenic trioxide is effective in the treatment of multiple myeloma in SCID mice, *Eur. J. Haematol.*, 72(3): 166-71 (2004).
Chu, "In Vitro Effects of Arsenic Trioxide on Head and Neck Squamous Cells Carcinoma", *Lifesci*, 45(01):0293 (2005).
Cui, et al., "Effects of Arsenic Trioxide on Protein Expressions of Related Genes in Vascular Endothelium Induced by Liver Cancer", Shijie Huaren Xiaohua Zazxhi, 13(9):1142-1144 (2005).

* cited by examiner

METHOD FOR INHIBITING CANCER USING ARSENIC TRIOXIDE

CROSS-REFERENCE TO RELATED APPLICATIONS

This application is a continuation in part of U.S. Ser. No. 10/669,869 filed Sep. 23, 2003, which claims priority to U.S. Ser. No. 60/417,200 filed Oct. 9, 2002 and U.S. Ser. No. 60/483,014 filed Jun. 25, 2003, and is also a continuation-in-part of 11/549,347 filed Oct. 13, 2006 and all of which are incorporated by reference in their entirety.

FIELD OF INVENTION

This invention relates to methods of inhibiting cancer by affecting expression, translation, and biological activity of cancers overexpressing or dependent on cyclin D1 using arsenic trioxide.

BACKGROUND OF THE INVENTION

Mantle cell lymphoma (MCL) is a well-defined subtype of B cell lymphoma in the World Health Organization classification, and accounts for approximately 3-10% of all non-Hodgkin lymphomas. The chromosomal aberration t(11;14)(q13;q32) can be found in practically all cases of MCL. The translocation results in juxtaposition of the immunoglobulin heavy chain joining region on chromosome 14 to the cyclin D1 gene on chromosome 11. The molecular consequence of the translocation is to place cyclin D1 under the control of the immunoglobulin heavy chain gene enhancer, leading to overexpression of the cyclin D1 protein.

Although MCL accounts for approximately 3-8% of B-cell lymphomas, it is difficult to manage. Initial treatment with rituximab plus combination chemotherapy or purine analogues results in complete remission (CR) rates varying from 34-87%. However, relapses occur in most patients with prolonged follow up. Treatment options for relapsed patients are limited. Several approaches have been adopted, including the use of the proteasome inhibitor bortezomib, thalidomide and the mammalian target of rapamycin (mTOR) inhibitor temsirolimus. The overall response (OR) rates of these agents varied from 38-81%, but the CR rate was only 3-31%. Therefore, there is an urgent need to define effective treatment strategies for MCL.

It is an object of this invention to provide agents and methods for treating cancers such as MCL and other cancers overexpressing cyclin D1.

It is another object of this invention to provide methods, strategies, doses, and dosing schedules for the administration of $As_2O_3$ in the clinical inhibition of cancers over-expressing cyclin D1.

SUMMARY OF THE INVENTION

It has been discovered that $As_2O_3$ suppresses cyclin D1 and initiates down-regulation of cyclin D1 by activating GSK-3 β, which phosphorylates cyclin D1. Activation of IKKb leads to phosphorylation of cyclin D1, which is ubiquitinated. Ubiquitinated cyclin D1 is degraded in the proteasome. This is the basis for the discovery that MCL and other cancers over-expressing cyclin D1 can be treated with $As_2O_3$, preferably oral $As_2O_3$.

BRIEF DESCRIPTION OF DRAWINGS

FIG. 2A: $As_2O_3$ (4 μM) induced a time dependent down-regulation of cyclin D1 in Jeko-1 and Granta-519 cells. Triplicate experiments and a representative Western blot demonstrate significant decrease in cyclin D1 level after 2 hours (one-way ANOVA with Dunnett's post-tests, $p<0.05$). FIG. 2B: $As_2O_3$ (treatment for 8 hours) induced a dose dependent down-regulation of cyclin D1 in Jeko-1 and Granta-519 cells. Triplicate experiments demonstrate significant decrease in cyclin D1 level at or above 2 μM (one-way ANOVA with Dunnett's post-tests, $p<0.05$).

FIG. 4A. Cell lysates immunoblotted with anti-phospho-cyclin D1 (Thr-286). $As_2O_3$ treatment led to significantly increased phosphor-cyclin D1 (triplicate experiments, one-way ANOVA with Dunnett's post-tests, $p<0.05$). FIG. 4B. Cell lysates immunoblotted with anti-phospho-cyclin GSK-3,p (Try-216). $As_2O_3$ treatment led to significantly increased phosphor-GSK-3β (triplicate experiments, one-way ANOVA with Dunnett's post-tests, $p<0.05$). FIG. 4C. Pre-incubation with 6-bromoindirubin-3'-oxime (BIO; 10 μM) before $As_2O_3$ treatment (4 μM, 8 hour, 37° C.) prevented cyclin D1 down-regulation, showing that GSK-3b was involved. Result a significant reduction of cyclin D1 as compared with control (triplicate experiments, one-way ANOVA with Dunnett's post-tests, $p<0.05$).

FIG. 5A. $As_2O_3$ treatment (4 μM for 2 hours) led to a significant increase in phosphor-IKKα/β (Ser-176/180) (triplicate experiments, one-way ANOVA with Dunnett's post-tests, $p<0.05$). FIG. 5B. Pre-incubation with the IKK inhibitor BMS (10 mM, 30 minutes) successfully prevented $As_2O_3$-induced cyclin D1 down-regulation (triplicate experiments, one-way ANOVA with Dunnett's post-tests, $p<0.05$).

FIGS. 7A and 713 show $As_2O_3$-induced cyclin D1 degradation involved the proteasome but not the lysosome in MCL. FIG. 7A. Pre-incubation with the proteasome inhibitors MG132 (MG, 30 μM), bortezomib (bort, 10 μg/ml) and lactacystin (lact, 10 μM) successfully prevented $As_2O_3$ induced cyclin D1 degradation.

DETAILED DESCRIPTION OF THE PREFERRED EMBODIMENTS

I. Arsenic Trioxide Formulations

Arsenic Trioxide

Figure 1A:
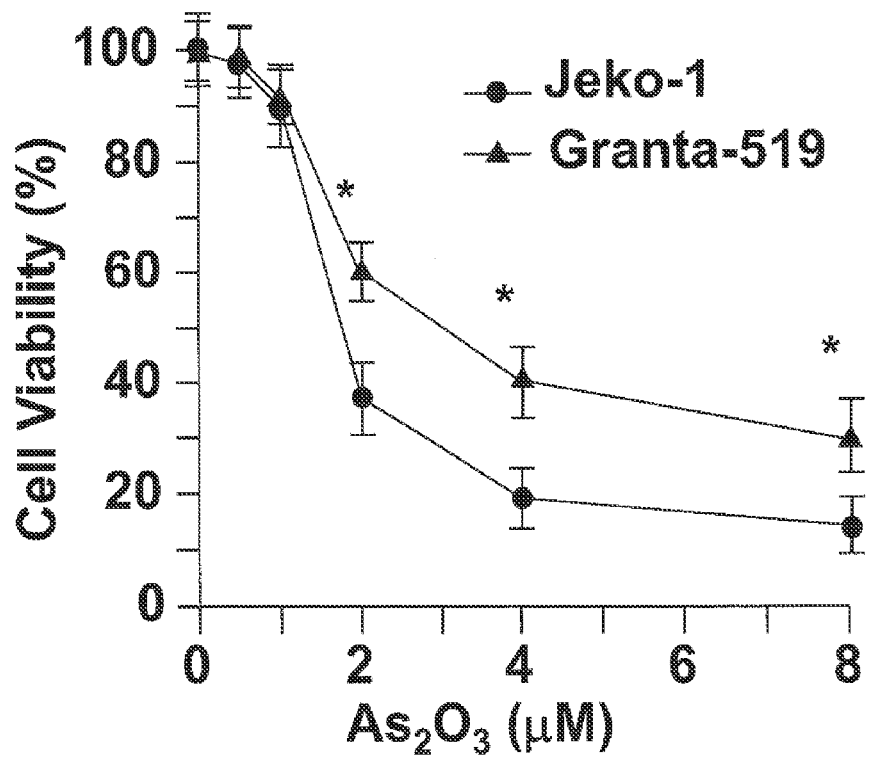
FIG. 1A is a line graph showing $As_2O_3$ (concentration in micromolar) percent induced apoptosis in MCL cells, based on a MTT test of Jeko-1 and Granta-519 cells treated for 72 hours with $As_2O_3$. There was a dose and time dependent suppression of cellular proliferation. Viability significantly decreased at or above 1 μM $As_2O_3$ as compared with baseline (one-way ANOVA with Dunnett's post-tests, $p<0.05$) (triplicate experiments)

Arsenic trioxide is available from a number of different suppliers. Arsenic trioxide is an amphoteric oxide which is known for its acidic properties. It dissolves readily in alkaline solutions to give arsenites. It is much less soluble in acids, but will dissolve in hydrochloric acid to give arsenic trichloride or related species. It reacts with oxidizing agents such as ozone, hydrogen peroxide and nitric acid to give arsenic pentoxide, $As_2O_5$. It is also readily reduced to arsenic, and arsine ($AsH_3$) may also be formed.

Arsenic trioxide has many uses including as: a starting material for arsenic-based pesticides; a starting material for arsenic-based pharmaceuticals, such as a neosalvarsan, a synthetic organoarsenic antibiotic; a decolorizing agent for glasses and enamels, a wood preservative, and a cytostatic in the treatment of refractory promyelocytic (M3) subtype of acute myeloid leukemia.

An oral arsenic trioxide ($As_2O_3$) is highly efficacious for relapsed acute promyelocytic leukemia. Oral $As_2O_3$ causes a smaller prolongation of QT intervals, and therefore is a much safer drug for treating leukemia.

Formulations

The following delivery systems, which employ a number of routinely used pharmaceutical carriers, are only representative of the many embodiments envisioned for administering the instant compositions.

Parenteral Formulations

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Enteral Formulations

Oral delivery systems include solid dosage forms such as tablets (e.g, compressed tablets, sugar-coated tablets, film-coated tablets, and enteric coated tablets), capsules (e.g., hard or soft gelatin or non-gelatin capsules), blisters, and cachets. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). The solid dosage forms can be coated using coatings and techniques well known in the art.

Oral liquid dosage forms include solutions, syrups, suspensions, emulsions, elixirs (e.g., hydroalcoholic solutions), and powders for reconstitutable delivery systems. The formulations can contain one or more carriers or excipients, such as suspending agents (e.g., gums, zanthans, cellulosics and sugars), humectants (e.g., sorbitol), solubilizers (e.g., ethanol, water, PEG, glycerin, and propylene glycol), surfactants (e.g., sodium lauryl sulfate, Spans, Tweens, and cetyl pyridine), emulsifiers, preservatives and antioxidants (e.g., parabens, vitamins E and C, and ascorbic acid), anti-caking agents, coating agents, chelating agents (e.g., EDTA), flavorants, colorants, and combinations thereof. The compositions can be formulated as a food or beverage (e.g., a shake) containing buffer salts, flavoring agents, coloring agents, sweetening agents, and combinations thereof.

Topical Formulations

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

II. Methods of Treatment

Cyclin D1 is a D-type cyclin critically involved in the control of the cell cycle. It assembles with its catalytic partners cyclin-dependent kinase 4 (CDK4) and CDK6 to form an active holoenzyme complex, which controls G1 progression and G1/S transition. The active holoenzyme complex phosphorylates the retinoblastoma protein RB. Phosphorylated RB releases the E2F family of transcription factors from inhibition, enabling E2Fs to coordinately regulate genes necessary for DNA replication and hence progression into S phase. Over-expression of cyclin D1 is demonstrable in many cancers, including cancers of the digestive tract, cancers of the female genital tract, and malignant lymphomas.

Owing to its important influence on the cell cycle, cyclin D1 expression is carefully regulated. Cyclin D1 gene mRNA and transcription appears to be constant through the cell cycle. However, a decline in cyclin D1 level occurs during S phase, which has been attributed to its increased proteasomal degradation. Cyclin D0 phosphorylation at a threonine residue 286 (Thr-286) positively regulates its proteasomal degradation. Thr-286 phosphorylation is mediated by glycogen synthase kinase-3β (GSK-3β). In addition to targeting cyclin D1 to proteosomes, GSK-3β-induced Thr-286 phosphorylation also promotes cyclin D1 nuclear export, by increasing the binding of cyclin D1 to a nuclear exportin CRM1. IkappaB kinase (IKK) alpha, IKKα, associates with and phosphorylates cyclin D1 also at Thr-286, thereby participating in the subcellular localization and turnover of cyclin D1.

$As_2O_3$ induced apoptosis in MCL lines at 2-4 μM, which is within the plasma levels achieved after $As_2O_3$ therapy. $As_2O_3$ induces a dose and time dependent suppression of cyclin D1. The suppression of cyclin D1 restores RB to a hypophosphorylated state, in parallel with a change in cell cycle. These biologic changes are consistent with the apoptosis observed upon $As_2O_3$ treatment.

The down-regulation of cyclin D1 mediated by $As_2O_3$ occurs at a post-transcriptional level since cyclin D1 is under the transcriptional control of the immunoglobulin heavy chain gene enhancer in MCL, which is unlikely to be affected by $As_2O_3$. Furthermore, in physiologic conditions, the control of cyclin D1 during the cell cycle is also mediated in part via alteration in the stability of cyclin D1. This process is controlled by phosphorylation of cyclin D1 at Thr-286, a process mediated by GSK-3β. GSK-3β is itself tightly regulated. Mitogens inactivate GSK-3β by a pathway involving Ras, phosphatidylinositol 3 kinase (PI3K), and protein kinaseB/Akt. Ras activates PI3K, which in turn activates Akt. Akt inactivates GSK-3β by phosphorylating it at serine residue 9. This removes the inhibition of GSK-3β on cyclin D1, allowing cyclin D1 to accumulate and thus activate cell cycling. GSK-3β can also be activated by phosphorylation at a tyrosine residue 216 (Try-216) in the kinase domain. $As_2O_3$-mediates an increase of GSK-30 Try-216 phosphorylation. The end result of $As_2O_3$-mediated increase in GSK-30 Try-216 phosphorylation is the increase in cyclin D1 Thr-286 phosphorylation, a key step in its degradation.

The IKK complex is the major regulatory component in the NK-κB pathway. It comprises the catalytic subunits IKKα and IKKβ, and a regulatory subunit IKKγ/NEMO. IKKα has been shown to phosphorylate cyclin D1 at Thr-286, the same site targeted by GSK-3b. IKKα needs to be activated by phosphorylation at a serine residue 176 (Ser-176) before participating in the regulation of NF-κB by phosphorylating IκB. IKKα Ser-176 phosphorylation is mediated by NK-κB inducing kinase (NIK). $As_2O_3$-induces an increase in IKK phosphorylation. $As_2O_3$-mediates an increase in physical interaction between IKK and cyclin D1, as shown in immunoprecipitation experiments. An IKK specific inhibitor BMS-345541 alleviated $As_2O_3$-induced cyclin D1 down-regulation. These results indicate that IKK is also an effector of $As_2O_3$ treatment.

$As_2O_3$-mediated cyclin D1 Thr-286 phosphorylation increases its ubiquitination. The time course of ubiquitination is commensurate with the timing of the biologic functions of $As_2O_3$ on the MCL lines. After $As_2O_3$ treatment, increased ubiquitination is first detected at 30 minutes and continues to increase. At two hours, significant down-regulation of cyclin D1 is first observed, which is associated with a parallel hypophosphorylation of RB. Significant activation of caspase 3 is observed at four hours. These sequence of events are consistent with cyclin D1 down-regulation initiated by Thr-286 phosphorylation.

Cyclin D1 is a cytosolic and nuclear protein. Therefore, polyubiquitination is involved, which targets the protein to degrade in proteasomes. Inhibition of proteasomes successfully prevented $As_2O_3$-induced down-regulation of cyclin D1. Inhibition of lysosomes, the site of degradation of monoubiquitinated proteins, does not interfere with $As_2O_3$-induced down-regulation of cyclin D1. These results confirm that $As_2O_3$ down-regulated cyclin D1 by promoting its proteasomal degradation.

Arsenic trioxide can be used for the treatment of cancers that are dependent on cyclin D1 for proliferation, survival, metastasis and differentiation.

Patients with cancers that overexpress cyclin D can be treated with $As_2O_3$. Mantle cell lymphoma is a cancer characterized by overexpression of cyclin D, as are cancers of the digestive tract, cancers of the female genital tract, and malignant lymphomas.

The dose of oral $As_2O_3$ is typically adjusted according to age and kidney function. In one embodiment, the dose range of $As_2O_3$ varies from 1 to 10 mg, typically about 5 to 10 mg.

The present invention will be further understood by reference to the following non-limiting examples.

EXAMPLES

Example 1

In Vitro Studies Show $As_2O_3$ is Effective in Treatment of MCL by Targeting Cyclin D1

Materials and Methods

Cell lines. The MCL lines Jeko-1 and Granta-519 were obtained from German Collection of Microorganisms and Cell Cultures (ACC 553 and ACC 342, Braunschweig, Germany). Jeko-1 cells were cultured in RPMI 1640 with 20% fetal bovine serum (FBS), and Granta-519 cells in DMEM with 10% FBS; both with 50 units/ml penicillin and 50 μg/ml streptomycin, at 5% $CO_2$.

Reagents and antibodies. Reagents and antibodies used included cell culture reagents (Invitrogen, Carlsbad, Calif., USA); kinase inhibitors and their inactive analogues (Calbiochem, Darmstadt, Germany); antiserum to phospho-GSK3 (tyrosine 216, Try-216) (Upstate, Lake Placid, N.Y., USA); antisera to cyclin D1, phospho-cyclin D1 (Thr-286), GSK3β, phospho-GSK3β (Tyr-216), IκB kinase (IKK)α/β, phospho-IKKα/β (serine 1761180, Ser-176/180), RB and phospho-RB (serine 795, Ser-795), caspase-3 and β-actin (Cell Signaling Technology, Beverly, Mass., USA); protein G-agarose (Upstate); ECL kit (Amersham, Piscataway, N.J., USA); cell proliferation kit I (MTT) (Roche Applied Science, Indianapolis, Ind., USA); annexin V-FITC Kit (Beckman Coulter, Fullerton, Calif., USA); and RNeasy Kit and One-Step RT-PCR Kit (Qiagen, Valencia, Calif., USA).

Cell viability assays. Cells were seeded on 96-well microplates at $2 \times 10^4$/well in 100 ml growth medium containing different concentration of $As_2O_3$ as indicated at 37° C. for 72 hours. MTT labeling reagent (10 μl, 5 mg/ml) (Roche Applied Science, Indianapolis, Ind., USA) was added to each well at 37° C. for 4 hours, followed by 100 μl solubilization at 37° C. overnight. Solubilized fomarzan crystals were quantified spectophotometrically at 590 nm with a microplate ELISA reader.

Apoptosis assay. Cells were seeded at $1 \times 10^6$/ml in different concentrations of $As_2O_3$ as indicated at 37° C. for 24 hours, harvested, rinsed in ice-cold phosphate buffered saline (PBS), and resuspended in 500 μl binding buffer containing annexin V-FITC and propidium iodide (PI) (Beckman Coulter, Fullerton, Calif., USA) for 20 minutes on ice. The percentages of apoptotic cells (annexin-V positive, PI negative) were determined on a flow cytometer (Epics, Beckman Coulter) with appropriate color compensation.

Cell Cycle Analysis. Cells were seeded at $1 \times 10^5$/ml in different concentrations of $As_2O_3$ as indicated at 37° C. for 8 hours, harvested, washed in ice-cold PBS, resuspended in 500 μl PBS, stained with PI for 10 minutes on ice. Cell cycle was determined by flow cytometry (Epics, Beckman Coulter).

Semi-quantitative reverse transcription polymerase chain reaction (RT-PCR) for cyclin D1. Cells were seeded at a density of $1 \times 10^6$/ml in different concentrations of $As_2O_3$ at 37° C. for 8 hours, washed with PBS buffer and lysed with RTL buffer. RNA was extracted with an RNeasy Kit, followed by cDNA synthesis and a 30-cycle PCR with a One-Step RT-PCR Kit with the forward primer 5'-CTG GCC ATG AAC TAC CTG GA-3' and the reverse primer 5'-GTC ACA CTT GAT CAC TCT GG-3'. Cycling conditions were denaturation (1 minute at 94° C., first cycle 5 minutes), annealing (2 minutes at 50° C.) and extension (3 minutes at 72° C., last cycle 10 minutes).

Western Blotting Analysis. Cells were seeded at a density of $1 \times 10^6$/ml overnight. Where applicable, cells were pretreated with various inhibitors for 30 minutes, and then incubated with 4 μM $As_2O_3$ for different time periods as indicated. Cells were lysed in lysis buffer (50 mM Tris-HCl, 100 mM NaCl, 5 mM EDTA, 40 mM $NaP_2O_7$, pH 7.5, 1% Triton X-100, 4 μg/ml aprotinin, 1 mM dithiothreitol, 200 μM $Na_3VO_4$, 0.7 μg/ml pepstatin, 100 μM phenylmethylsulfonyl fluoride, and 2 μg/ml leupeptin). Clarified lysates were resolved on 12% SDS-phenylmethylsulfonyl fluoride and transferred to nitrocellulose membranes. The membranes were blocked with 5% non-fat milk, washed, incubated with the appropriate antibodies followed by horseradish peroxidase-conjugated secondary antisera. Immuno-reactive bands were visualized by chemiluminescence with the ECL kit, detected on X-ray films and quantified by densitometric scanning (Eagle Eye II still video system, Stratagene, La Jolla, Calif., USA).

Coimmunoprecipitation Assays. Cells were seeded at $1 \times 10^6$/ml overnight, treated with 4 µM $As_2O_3$ at 37° C. for different time periods as indicated, and lysed in lysis buffer, Cell lysates were incubated with an anti-cyclin D1, anti-ubiquitin, anti-calpain 2 or anti-IKKα/β antibodies (4 µg/sample) at 4° C. for 1 hour, followed by incubation with 30 µl of protein G-agarose (50% slurry) at 4° C. for another 2 hour. Immunoprecipitates were washed four times with 400 µl lysis buffer, resuspended in 50 µl lysis buffer and 10 ml 6× sample buffer and boiled for 5 minutes. Immunoprecipitates were then analysed by Western blot analysis.

Results $As_2O_3$ induced dose and time dependent apoptosis in MCL cells.

The MTT test showed that $As_2O_3$ induced a dose-dependent cytotoxicity in Jeko-1 and Granta-519 cells. Flow cytometric analysis showed that $As_2O_3$ treatment led to induction of apoptosis. Western blot analysis showed that caspase 3 activation was involved in $As_2O_3$-induced apoptosis.

Figure 1B:
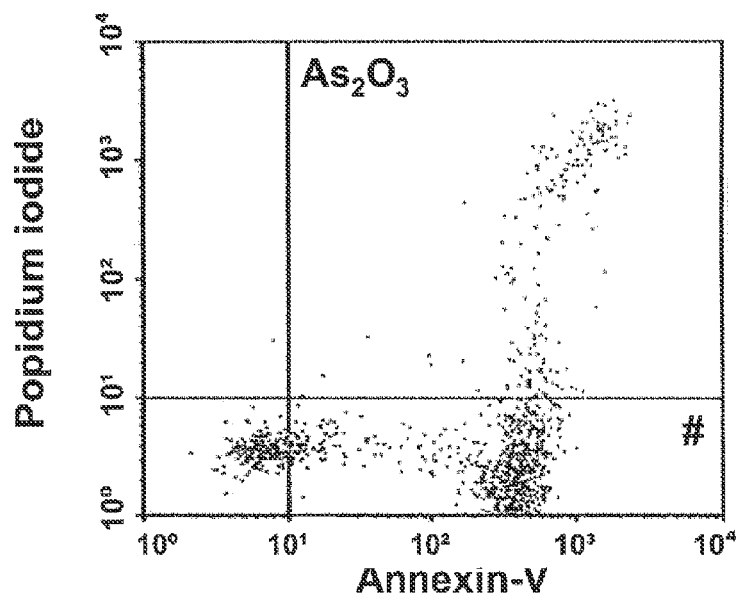
FIG. 1B is a scatter plot of popidium iodide versus annexin expression in cells treated with $As_2O_3$. There was a significant increase in apoptotic cells after $As_2O_3$ treatment. (#: apoptotic cells that were annexin V positive and popidium iodide negative).
Figure 2A:
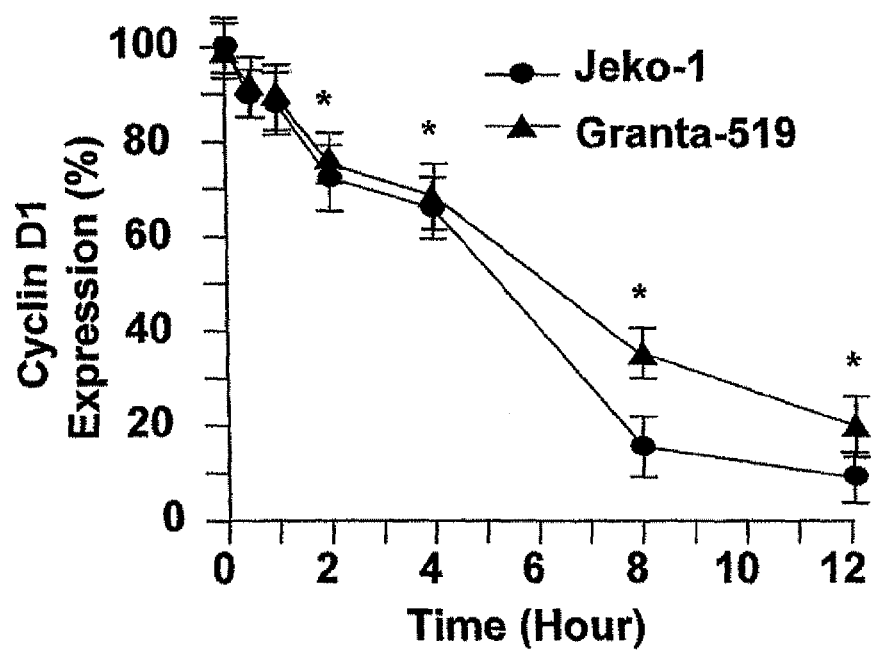
FIGS. 2A and 2B show down-regulation of cyclin D1 by $As_2O_3$ treatment.
Figure 2B:
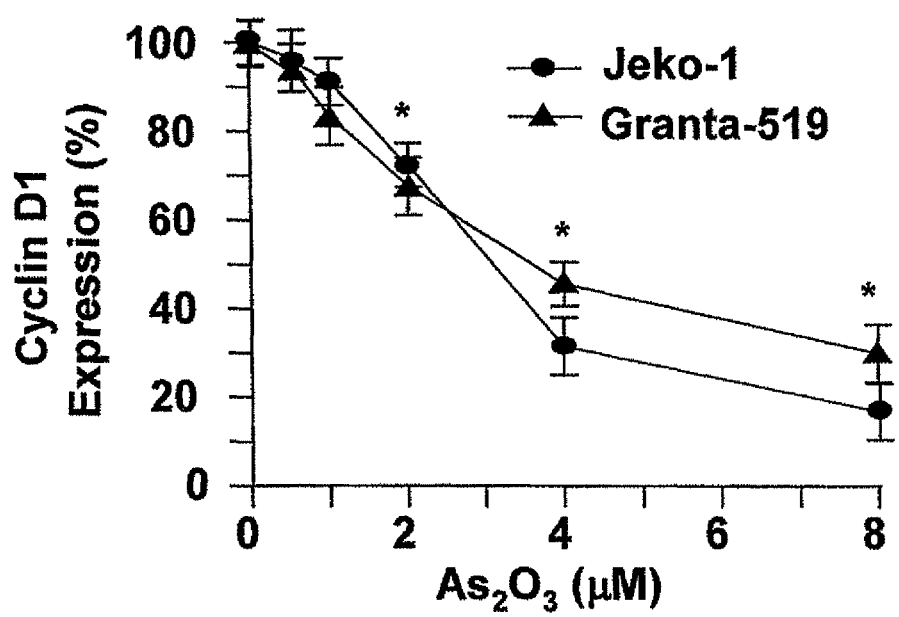
Figure 3:
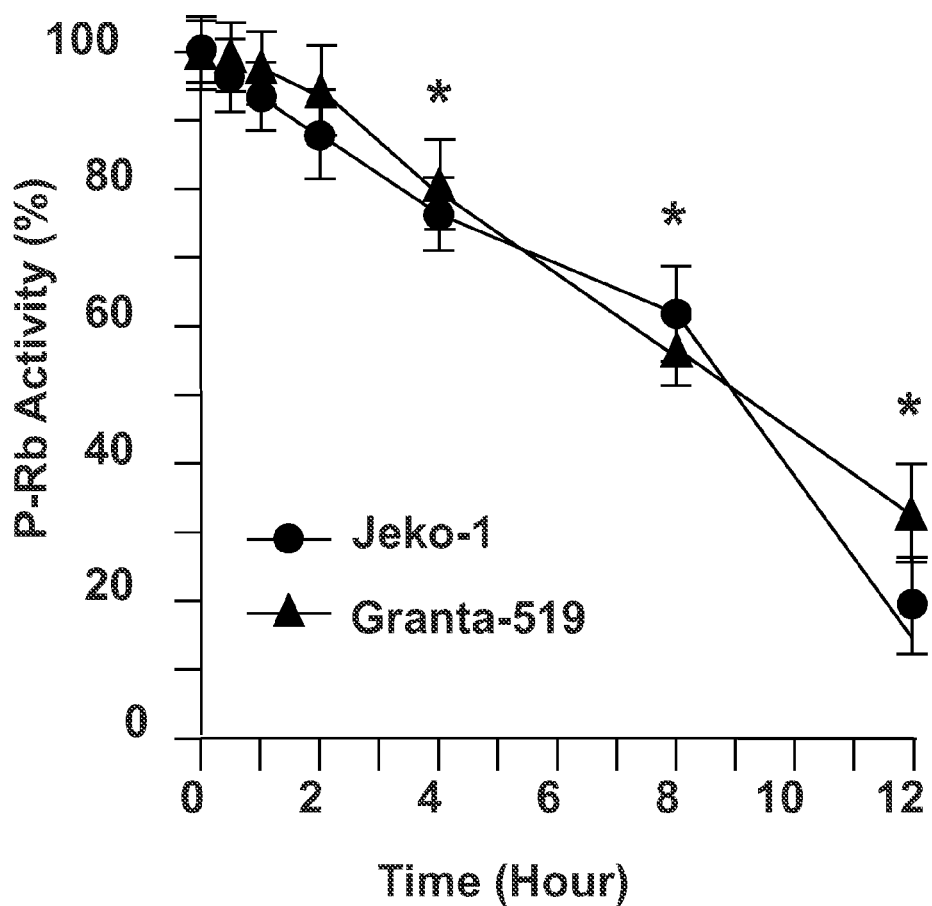
FIG. 3 shows dephosphorylation of retinoblastoma (RB) by $As_2O_3$ treatment in MCL lines. $As_2O_3$ treatment resulted in dephosphorylation of RB (significant decrease of phosphor-Rb Ser-795 at or more that 8 hours of $As_2O_3$ treatment, triplicate experiments, one-way ANOVA with Dunnett's post-tests, $p<0.05$).
Figure 4:
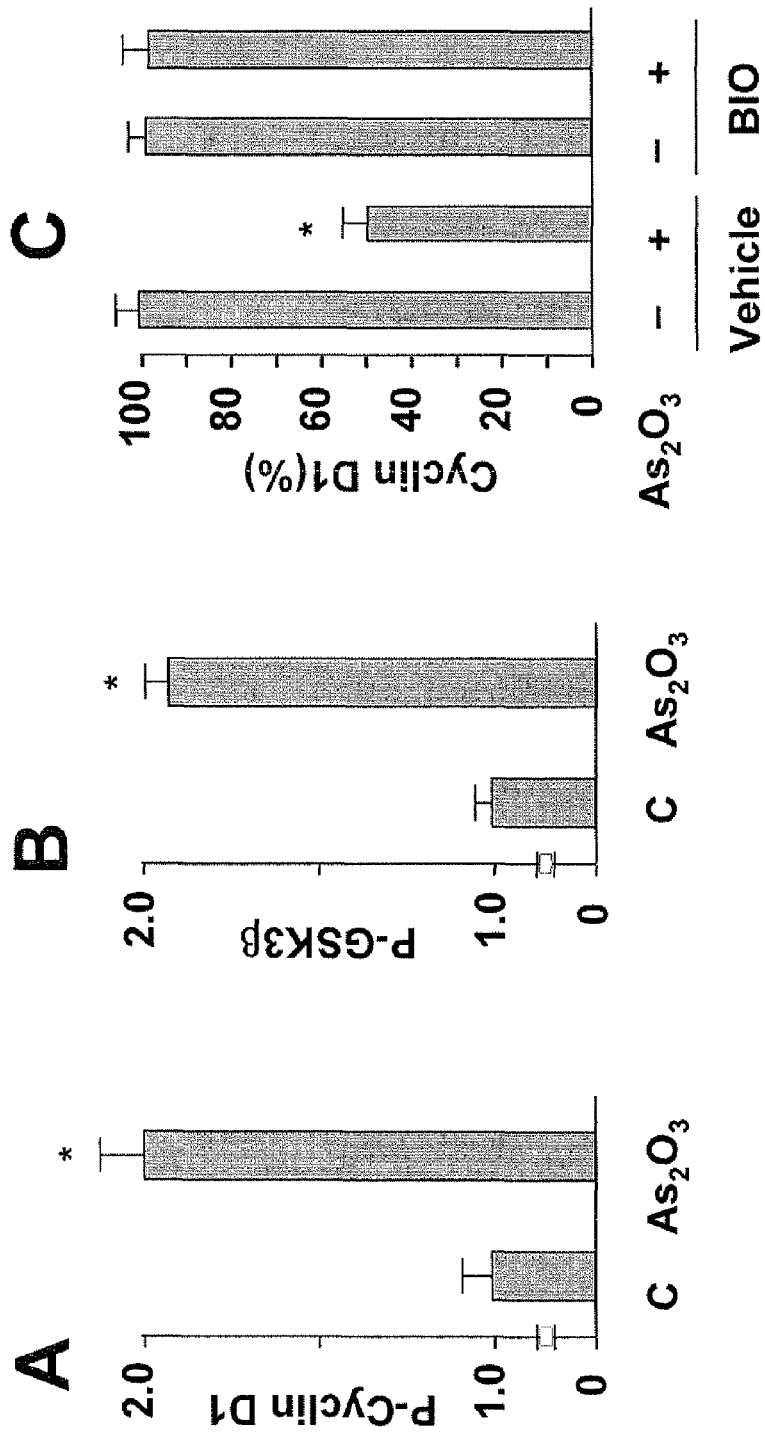
FIGS. 4A, 4B and 4C show $As_2O_3$ treatment induced phosphorylation of cyclin D1 and GSK-3.

FIGS. 1A and 1B are graphs showing $As_2O_3$ (concentration in microM) percent induced apoptosis in MCL cells measured using a MTT test of Jeko-1 and Cranta-519 cells treated for 72 hours with $As_2O_3$. There was a dose and time dependent suppression of cellular proliferation. Viability significantly decreased at or above 1 µM $As_2O_3$ as compared with baseline (one-way ANOVA with Dunnett's post-tests, $p<0.05$) (triplicate experiments). (. Significant increase in apoptotic cells after $As_2O_3$ treatment. #: apoptotic cells that were annexin V positive and popidium iodide negative). Western Blotting showed activation of caspase 3 by $As_2O_3$ treatment, 0, 1.5 and 2.5 microM. Cleaved caspase 3 were detectable four hours after $As_2O_3$ treatment.

Cyclin D1 was down-regulated in MCL by $As_2O_3$. To determine the molecular mechanisms of $As_2O_3$-induced apoptosis in MCL, the expression of cyclin D1 was examined. Western blot analysis showed that $As_2O_3$-induced a time and dose dependent suppression of cyclin D1 in both Jeko-1 and Granta-519 cell lines. Treatment with $As_2O_3$ at 4 µM led to suppression of cyclin D1, first detectable at 2 hours and almost complete at 8-12 hours $As_2O_3$ suppression of cyclin D1 was also dose-dependent. Triplicate experiments demonstrate significant decrease in cyclin D1 level after 2 hours (one-way ANOVA with Dunnett's post-tests, $p<0.05$) Triplicate experiments demonstrate significant decrease in cyclin D1 level at or above 2 µM (one-way ANOVA with Dunnett's post-tests, $p<0.05$). Semi-quantitative polymerase chain reaction showing that cyclin D1 gene transcription was unaffected by $As_2O_3$ treatment.

$As_2O_3$ induced down-regulation of cyclin D1 disrupted its signaling. To investigate if cyclin D1 down-regulation is biologically relevant, RB phosphorylation was investigated. $As_2O_3$ treatment led to a time dependent decrease in RB phosphorylation, which occurred at a similar time-frame as compared with cyclin D1 down-regulation. Cell cycle analysis by flow cytometry showed that there was an increase in the proportion of apoptotic cells.

Down-regulation of cyclin D1 by $As_2O_3$ was post-transcriptional. RT-PCR showed that cyclin-D1 gene transcription was unaffected by $As_2O_3$ treatment of up to 8 µM, suggesting that the down-regulation of cyclin D1 was post-transcriptional.

$As_2O_3$-induced cyclin D1 down-regulation was related to GSK3β activation. Western blot analysis showed that $As_2O_3$ treatment resulted in significant increases in cyclin D1 phosphorylation at Thr-286, a prerequisite for cyclin D1 degradation. Cyclin D1 phosphorylation by GSK-3β requires prior activation of GSK-3β by phosphorylation at Tyr-216. $As_2O_3$ treatment significantly increased GSK-3β Tyr-216 phosphorylation, indicating that GSK-3β might mediate $As_2O_3$-induced cyclin D1 phosphorylation and hence degradation. To confirm the role of GSK-3β as a mediator of $As_2O_3$, Jeko-1 cells were pre-incubated with the GSK-3β inhibitor 6-bromoindirubin-3'-oxime (BIO; 10 µM) before $As_2O_3$ treatment. The results showed that BIO successfully prevented $As_2O_3$-induced down-regulation of cyclin D1. Collectively, these observations indicate that $As_2O_3$ down-regulated cyclin D1 post-transcriptionally, probably by increasing its degradation.

Figure 5A:
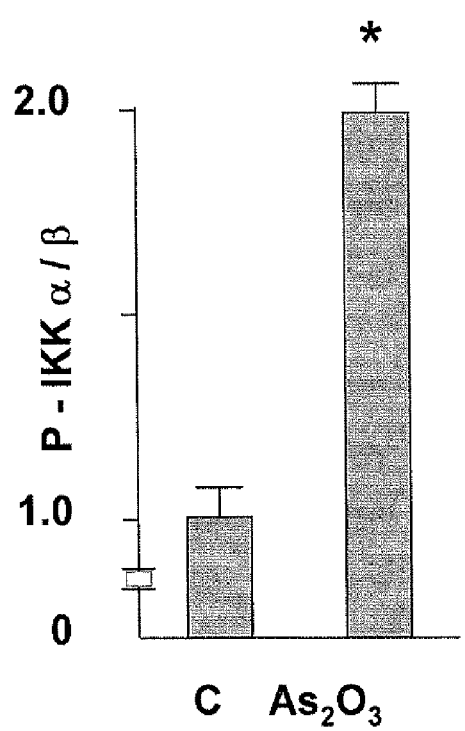
FIGS. 5A and 5B show that IKK was involved in $As_2O_3$-induced down-regulation of cyclin D1.
Figure 5B:
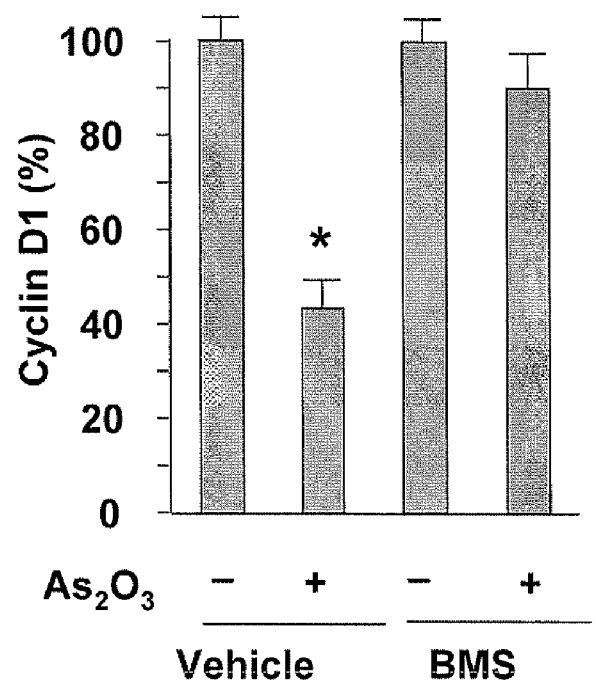

$As_2O_3$-induced cyclin D1 down-regulation was also dependent on IKKα/β. To determine if IKK was involved in $As_2O_3$-induced down-regulation of cyclin D1, IKKα/β phosphorylation at Ser-178/180 was examined. $As_2O_3$ significantly increased IKKα/β Ser-178/180 phosphorylation, which was required for activation of IKKα/β (FIG. 5A). Pre-treatment with the IKKα/β inhibitor BMS-345541 (BMS; 10 µM) significantly prevented $As_2O_3$-induced cyclin D1 down-regulation, suggesting that IKKα/β was a molecular mediator of $As_2O_3$ (FIG. 5B). Immunoprecipitation with an anti-IKKα/β antibody showed that cyclin D1 bound IKKα/β. Similarly, when cyclin D1 was immunoprecipitated, IKKα/β was also confirmed to co-immunoprecipitate. These results confirmed that $As_2O_3$ activated IKKα/β, which participated in the down-regulation of cyclin D1.

Figure 6:
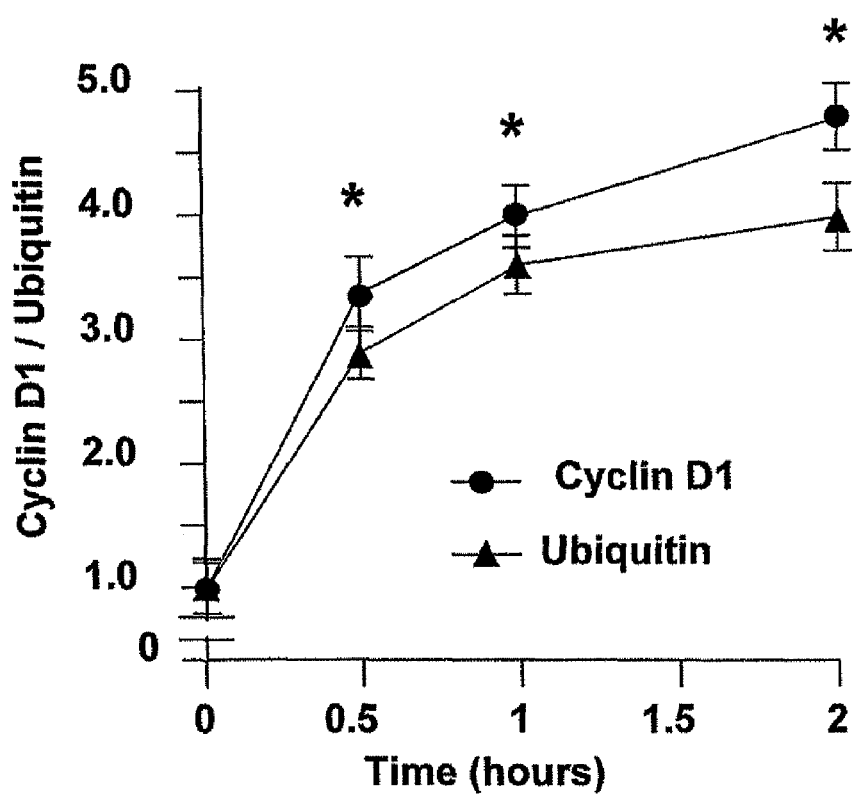
FIG. 6 shows $As_2O_3$-induced ubiquitination of cyclin D1 in MCL. Cell lysates were immunoprecipitation with anti ubiquitin (Ub) or anti-cyclin D1 antibody. The immunoprecipitates and the crude lysates were immunoblotted with anti-cyclin D1 and anti-ubiquitin antisera. $As_2O_3$ induced a significant increase in binding between cyclin D1 and ubiquitin (increase in ubiquitination from 30 minutes to 2 hours after $As_2O_3$ treatment as compared to the baseline, triplicate experiments, one-way ANOVA with Dunnett's post-tests, $p<0.05$).

$As_2O_3$ promoted cyclin D1 ubiquitination. To study if $As_2O_3$-induced cyclin D1 down-regulation was mediated via ubiquitination, immunoprecipitation experiments were performed on lysates from Jeko-1 cells treated with $As_2O_3$. Immunoprecipitation with an anti-ubiquitin antibody showed a time-dependent increase in bound cyclin D1 (FIGS. 6A and B). Similarly, lysates immunoprecipitated with an anti-cyclin D1 antibody also showed a time dependent increase in bound ubiquitin. These results showed that $As_2O_3$ promoted cyclin D1 ubiquitination, confirming that $As_2O_3$-induced GSK-31 and IKKα/β activation was biologically relevant.

Figure 7A:
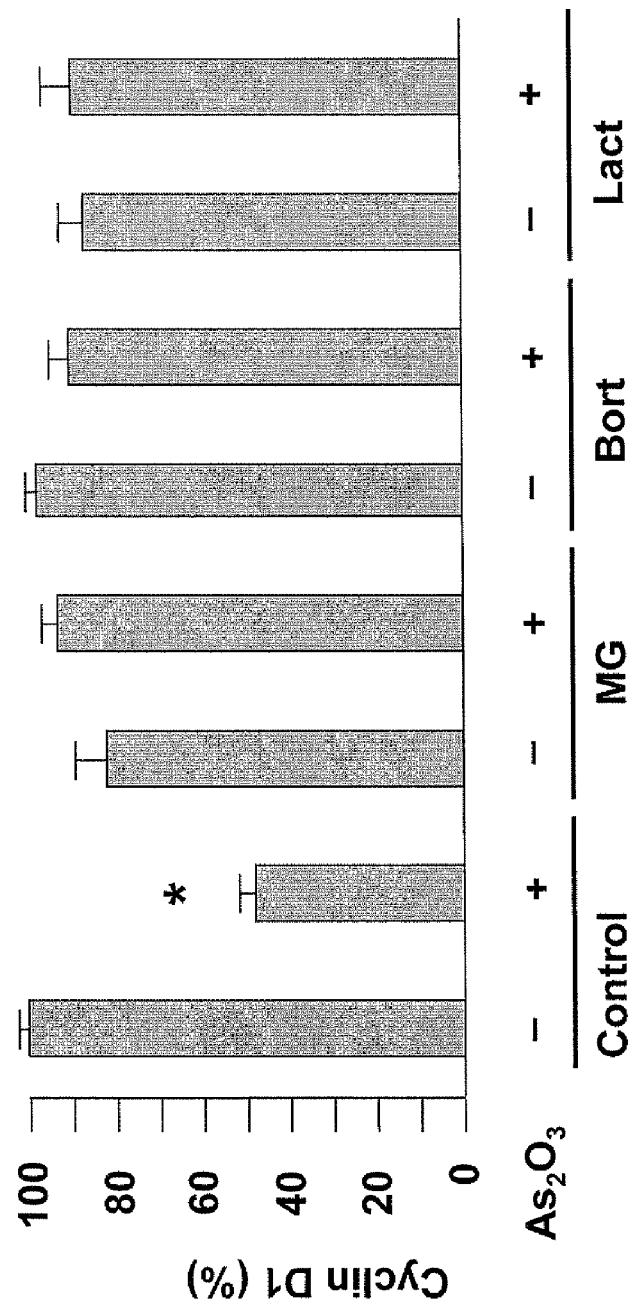
Figure 7B:
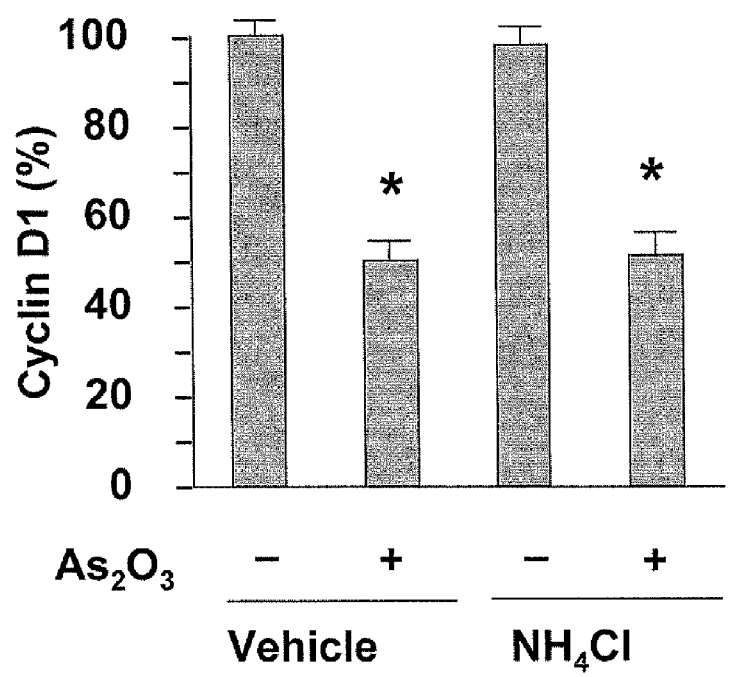
FIG. 7B. Pre-incubation with the lysosomal inhibitor ammonium chloride ($NH_4Cl$, 2.5 mM) was ineffective in preventing $As_2O_3$-induced cyclin D1 degradation.

$As_2O_3$ induced cyclin D1 degradation in 26S and 20S proteasomes but not lysosomes. Pre-incubation of Jeko-1 cells with the 26S and 20S proteosome inhibitors MG132 (30 µM), bortezimab (10 µg/ml) and lactacystin (10 µM) attenuated $As_2O_3$-induced cyclin D1 down-regulation (FIG. 7A). However, pre-incubation with the lysosomal inhibitor ammonium chloride ($NH_4Cl$) had no effect on $As_2O_3$-induced down-regulation of cyclin D1 (FIG. 7B). The results confirmed that $As_2O_3$ down-regulated cyclin D1 by promoting its ubiquitination, hence targeting it to the proteosome for degradation.

Figure 8:
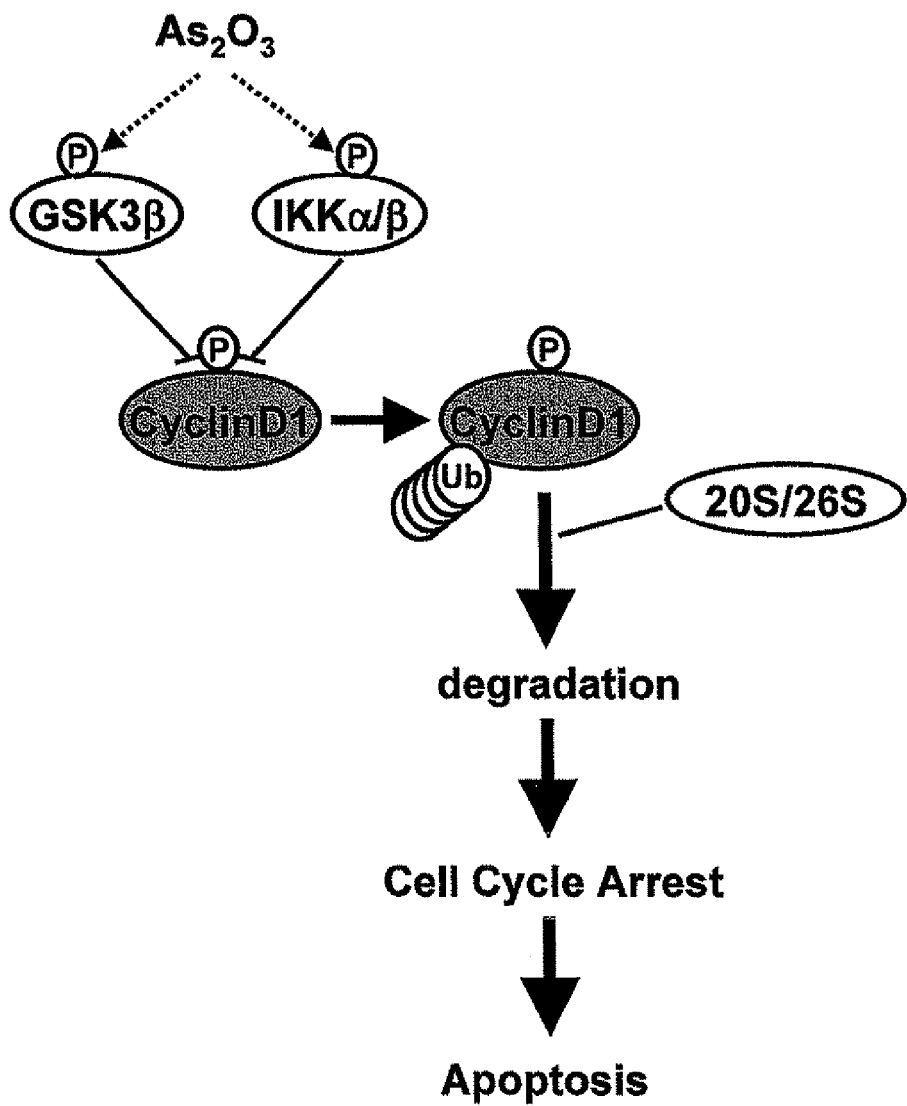
FIG. 8 is a schematic diagram showing the proposed mechanism of degradation of cyclin D1 mediated by $As_2O_3$.

Overall model. An overall model of the action of $As_2O_3$ on MCL is shown in FIG. 8.

Example 2

Clinical Study of Oral-$As_2O_3$ in the Treatment of Patients with Refractory and Relapsed MCL that Over-Expressed Cyclin D1

Materials and Methods

Patients. Consenting patients with relapsed or refractory B-cell lymphomas, and an ECOG performance status of <2 were recruited. All patients gave informed consent, and the treatment was approved by the institute review board of Queen Mary Hospital.

Treatment. Treatment was initiated with oral-$As_2O_3$ (10 mg/day for patients below 70 years old with normal renal function; 5 mg/day for patients over 70 years old, or with impaired renal function), ascorbic acid (AA, 1 g/day) and chlorambucil (4 mg/day) as outpatients until disease response multi-agent chemotherapy. Other previous treatment included rituximab (n=8), autologous hematopoietic stem cell transplantation (HSCT) (n7-3), and bortezomib (n=1). Other poor prognostic indicators included marrow infiltration (n=11) and extensive extranodal involvement (n=9), so that 12/14 (86%) cases had stage IV disease. The median time from initial diagnosis to $As_2O_3$ treatment was 33 (8-85) months.

TABLE 1

Clinicopathologic features and treatment outcome of 14 patients with relapsed or refractory MCL

| | | Initial disease | | | Current relapse | | Total | | Outcome and |
|---|---|---|---|---|---|---|---|---|---|
| | | stage | sites | Previous treatment | Time* | No Sites | $As_2O_3$ | response | survival |
| 1 | M/69 | III | Colon, abdomen | FND × 6, COPP × 6 | 56 m | 2 Cervical | 140 mg | CR | off Rx, 28 m+. |
| 2 | M/63 | IV | BM, generalized LN | R-CEOP × 6, IMVP × 6 | 11 m | 2 BM, cervical | 160 mg | CR | on Rx, 13 m+. |
| 3 | M/65 | IV | BM, mesentery, generalized LN | FND × 7, IMVP × 2, R-DHAP × 8 | 85 m | 3 Eye | 120 mg | CR | on Rx, 17 m+. |
| 4 | F/77 | IV | Pleura, generalized LN | Clb | 33 m | 1 Groin, jaw | 140 mg | CR | R2 at 16 m, CR again with $As_2O_3$ + Clb |
| 5 | M/70 | III | Generalized LN | COPP × 2, IMVP × 6, Clb | 85 m | 4 Cervical, abdomen | 250 mg | CRu | R5 at 20 m, on $As_2O_3$ + Clb |
| 6 | M/76 | IV | BM, generalized LN | CEOP × 7 | 19 m | 1 BM, leukemic, eyes, generalized LN | 210 mg* | CRu | on Rx, 8 m+ |
| 7 | M/58 | IV | BM, generalized LN | CEOP × 6, R-ESHAP × 6 | 18 m | 2 Generalized skin | 140 mg | PR | On Rx, 3 m+ |
| 8 | M/81 | IV | BM, leukemic, liver, spleen | CHOP × 6, ChlVPP × 2 | 18 m | 2 BM, LN, liver, spleen, leukemic | 300 mg* | PR | died at 16 m |
| 9 | M/51 | IV | Generalized LN, spleen, BM, scalp, eye | CVAD × 7, CEOP × 2, R-DHAP × 3, Thal | 25 m | 4 BM, LN, scalp | NA* | Static | on Rx, 8 m+ |
| 10 | F/76 | IV | General LN, BM, scalp | R-COPP × 6 | 12 m | 2 BM, LN | 160 mg* | PR | died at 6 m |
| 11 | M/90 | IV | BM, leukemic | Clb | 8 m | 1 BM, leukemic | NA | NR | died at 4 m |
| 12 | M/54 | IV | Generalized LN, BM, gut, liver, spleen, leukemic | CEOP × 6, DHAP × 1, NOPP × 5, Clb | 36 m | 3 BM, generalized LN, spleen | NA | Static | died at 17 m |
| 13 | F/57 | IV | Generalized LN, BM, spleen | CEOP × 6, DHAP × 4, R-BVP × 3 | 36 m | 3 BM, LN | NA | NR | died at 1 m |
| 14 | M/63 | IV | Generalized LN, pleura, BM | CEOP × 6, AHSCT, R-DHAP × 6, Thal, velcade, FND | 72 m | 3 BM, generalized LN | NA | NR | died at 1 m |

M: male; F: female; LN: lymphadenopathy; BM: bone marrow; m: months; R: rituximab; CEOP: cyclophospamide, epirubicin, vincristine, predniolone
FND: fludarabine, mitoxantrone, dexamethasone; DHAP: cisplatinum, cytosine arabinoside, dexamethasone; Thal: thalidomide
ChlvPP: chlorambucil, vincristine, procarbazine, prednisolone; COPP: cyclophosphamide, vincristine, procarbazine, prednisolone; NOPP: mitoxantrone; vincristine, procarbazine, prednisolone; BVP; bleomycin, vinblastine, prednisolone; AHSCT: autologous hematopoietic stem cell transplantation
Clb: chlorambucil; NA: not available; CR: complete remission; CRu: complete remission (unconfirmed); PR: partial remission; NR; no response or progression was documented. In patients with bulky disease, debulking with VPP (vincristine 2 mg/day×1, prednisolone 30 mg/day×14 and procarabzine 50-100 mg/day×14) was used. After maximum response was achieved, chlorambucil was taken off and a maintenance regimen of $As_2O_3$ (5-10 mg/day) and AA (1 g/day) was given for two weeks every 2 months for a planned two years. Responses were classified according to standard NCI criteria, and monitored by regular physical examination, marrow and blood assessment, and computerized tomographic scans.

Results

Characteristics of patients with MCL. Table 1 shows the results of the clinical use of oral-$As_2O_3$ in patients with refractory or relapsed mantle cell lymphoma that over-expressed cyclin D1. The results showed an overall response rate of 64%. Four patients achieved complete remission (CR), whereas two patients achieved complete remission unconfirmed. Of the fourteen patients treated (Table 1), eleven had advanced relapses (R) (R2, n=5; R3, n=4; R4, n=2). Three patients treated in R1 had advanced age (76, 77 and 90 years). All but two patients had received an anthracycline based Treatment response. Nine patients responded, giving an OR rate of 64%. Four patients (cases 1-4) achieved CR. Two patients (cases 5, 6) achieved unconfirmed CR (CRu). They had become asymptomatic without any detectable superficial diseases. Marrow and peripheral blood involvement was also cleared. However, small residual internal lymph nodes remained. These lymph nodes were negative on gallium scan and had remained static in size. Three patients had partial responses (PR) with >50% reduction in the size of assessable lymph nodes.

Case 6 had bilateral orbital infiltration at relapse that completely resolved after 4 months of oral $As_2O_3$ treatment and ascorbic acid. Case 8 who was relapsing in leukemic phase with massive splengomegaly showed partial remission after 8 months of treatment with oral $As_2O_3$ and ascorbic acid as determined by MRI scans. Histological analysis revealed that case X had dense marrow infiltration that resolved after 8 months of treatment with oral-$As_2O_3$ and ascorbic acid.

Outcome. Of the four patients with CR, one had relapsed at 16 months. She achieved a CR3 again with daily $As_2O_3$ and resumption of chlorambucil. Two patients were still on maintenance $As_2O_3$+AA treatment, while one had completed the planned two years of treatment. Of the two patients with CRu, one patient had relapsed at 20 months. He achieved CR5 again with $As_2O_3$ and chlorambucil therapy. For the three patients with PR, one patient developed progressive disease while on maintenance therapy 12 months later and died of refractory lymphoma. Two defaulted treatment and both relapsed.

Toxicity. Significant (W.H.O grade 3-4) neutropenia and thrombocytopenia was observed in 7 patients. These patients had previously received multiple chemotherapy, or autologous HSCT. The neutropenia responded to hematopoietic growth factors. No significant sepsis or bleeding were observed. Other side effects included fever (n=7), herpes zoster reactivation (n=3), fluid accumulation (n=2), nausea (n=3) and headache (n=2). No significant QT prolongation or arrhythmia was observed. Five patients did not report any side effects at all.

$AS_2O_3$ suppresses MCL cell growth by targeting cyclin D1. $AS_2O_3$ induces the phosphorylation of GSK-3 p and IKK. Cyclin D1 over-expression is pathogenetically important in a vast diversity of cancers. Oral-$As_2O_3$ inhibited refractory or relapsed MCL in 14 patients, which over-expressed cyclin D1, with an overall response in 9 patients (64%). Four patients achieved complete remission, two patients complete remission unconfirmed, and three patients with partial remissions. These results were very good, given that these patients had refractory or relapsed disease.

Taken together, the evidence demonstrates that $As_2O_3$ decreases cyclin D1 and that the decrease in cyclin D1 was post-transcriptional. $As_2O_3$ induces GSK-3β and IKK activation and hence phosphorylation of cyclin D1. Phosphorylated cyclin D1 is degraded in the proteasome. Oral $As_2O_3$ induces a high response rate clinically in patients with refractory or relapsed MCL, a cancer that over-expresses cyclin D1.

I claim:

1. A method for treating lymphoma in a subject comprising orally administering to the subject an effective amount of arsenic trioxide to inhibit lymphoma cells.

2. The method according to claim 1, wherein the effective amount of arsenic trioxide is from 1 to 10 mg/day.

3. The method of claim 1 wherein the lymphoma goes into complete remission.

4. The method of claim 1, wherein the lymphoma cells are mantle cell lymphoma cells.

\* \* \* \* \*